US007758604B2

United States Patent
Wu et al.

(10) Patent No.: US 7,758,604 B2
(45) Date of Patent: Jul. 20, 2010

(54) CUTTING BALLOON CATHETER WITH IMPROVED BALLOON CONFIGURATION

(75) Inventors: Show-Mean Steve Wu, San Diego, CA (US); Ricardo David Roman, San Diego, CA (US); Reynaldo Cruz, National City, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 64 days.

(21) Appl. No.: 10/447,766

(22) Filed: May 29, 2003

(65) Prior Publication Data

US 2004/0243156 A1 Dec. 2, 2004

(51) Int. Cl.
  *A61B 17/22* (2006.01)
(52) U.S. Cl. .................. 606/191; 606/159; 606/108
(58) Field of Classification Search .......... 606/159; 604/103, 103.08
See application file for complete search history.

(56) References Cited

U.S. PATENT DOCUMENTS

| 2,816,552 | A | 12/1957 | Hoffman |
| 3,174,851 | A | 3/1965 | Buehler et al. |
| 3,351,463 | A | 11/1967 | Rozner et al. |
| 3,635,223 | A | 1/1972 | Klieman |
| 3,749,085 | A | 7/1973 | Willson et al. |
| 3,753,700 | A | 8/1973 | Harrison et al. |
| 3,990,453 | A | 11/1976 | Douvas et al. |
| 4,140,126 | A | 2/1979 | Choudhury |
| 4,141,364 | A | 2/1979 | Schultze |
| 4,263,236 | A | 4/1981 | Briggs et al. |
| 4,273,128 | A | 6/1981 | Lary |
| 4,292,974 | A | 10/1981 | Fogarty et al. |
| 4,406,656 | A | 9/1983 | Hattler et al. |
| 4,465,072 | A | 8/1984 | Taheri |
| 4,490,421 | A | 12/1984 | Levy |
| 4,572,186 | A | 2/1986 | Gould et al. |
| 4,574,781 | A | 3/1986 | Chin |
| 4,608,984 | A | 9/1986 | Fogarty |
| 4,627,436 | A | 12/1986 | Leckrone |
| 4,685,458 | A | 8/1987 | Leckrone |
| 4,686,982 | A | 8/1987 | Nash |

(Continued)

FOREIGN PATENT DOCUMENTS

DE   34 00 416 A1   7/1985

(Continued)

OTHER PUBLICATIONS

Lary, Banning G., et al., "A Method for Creating a Coronary-Myocardial Artery," *Surgery*, Jun. 1966, vol. 59, No. 6, pp. 1061-1064.

(Continued)

*Primary Examiner*—Corrine M McDermott
*Assistant Examiner*—Christopher D Prone
(74) *Attorney, Agent, or Firm*—Crompton, Seager & Tufte, LLC

(57) ABSTRACT

An angioplasty balloon catheter and method of making and using the same. The balloon catheter may include a catheter shaft and a balloon coupled to the shaft. The balloon may include one or more cutting edges or member and may include one or more wings. The wings may include an undulating surface.

5 Claims, 6 Drawing Sheets

U.S. PATENT DOCUMENTS

| | | | |
|---|---|---|---|
| 4,696,667 A | 9/1987 | Masch | |
| 4,705,517 A | 11/1987 | DiPisa, Jr. | |
| 4,723,549 A | 2/1988 | Wholey et al. | |
| 4,728,319 A | 3/1988 | Masch | |
| 4,747,405 A | 5/1988 | Leckrone | |
| 4,748,982 A | 6/1988 | Horzewski et al. | |
| 4,781,186 A | 11/1988 | Simpson et al. | |
| 4,784,636 A | 11/1988 | Rydell | |
| 4,787,388 A | 11/1988 | Hofmann | |
| 4,790,813 A | 12/1988 | Kensey | |
| 4,793,348 A | 12/1988 | Palmaz | |
| 4,796,629 A | 1/1989 | Grayzel | |
| 4,799,479 A | 1/1989 | Spears | |
| RE32,983 E | 7/1989 | Levy | |
| 4,867,157 A | 9/1989 | McGurk-Burleson et al. | |
| 4,886,061 A | 12/1989 | Fischell et al. | |
| 4,896,669 A | 1/1990 | Bhate et al. | |
| 4,909,781 A | 3/1990 | Husted | |
| 4,921,483 A | 5/1990 | Wijay et al. | |
| 4,921,484 A | 5/1990 | Hillstead | |
| 4,936,845 A | 6/1990 | Stevens | |
| 4,960,410 A | 10/1990 | Pinchuk | |
| 4,966,604 A | 10/1990 | Reiss | |
| 4,986,807 A | 1/1991 | Farr | |
| 4,994,018 A | 2/1991 | Saper | |
| RE33,561 E | 3/1991 | Levy | |
| 5,009,659 A | 4/1991 | Hamlin et al. | |
| 5,015,231 A | 5/1991 | Keith et al. | |
| 5,030,201 A | 7/1991 | Palestrant | |
| 5,041,125 A | 8/1991 | Montano, Jr. | |
| 5,042,985 A | 8/1991 | Elliott et al. | |
| 5,047,040 A | 9/1991 | Simpson et al. | |
| 5,053,007 A | 10/1991 | Euteneuer | |
| 5,053,044 A | 10/1991 | Mueller et al. | |
| 5,071,424 A | 12/1991 | Reger | |
| 5,074,841 A | 12/1991 | Ademovic et al. | |
| 5,074,871 A | 12/1991 | Groshong | |
| 5,078,722 A | 1/1992 | Stevens | |
| 5,078,725 A | 1/1992 | Enderle et al. | |
| 5,084,010 A | 1/1992 | Plaia et al. | |
| 5,085,662 A | 2/1992 | Willard | |
| 5,087,246 A | 2/1992 | Smith | |
| 5,087,265 A | 2/1992 | Summers | |
| 5,100,424 A | 3/1992 | Jang et al. | |
| 5,100,425 A | 3/1992 | Fischell et al. | |
| 5,102,390 A | 4/1992 | Crittenden et al. | |
| 5,102,403 A | 4/1992 | Alt | |
| 5,116,318 A | 5/1992 | Hillstead | |
| 5,135,482 A | 8/1992 | Neracher | |
| 5,147,302 A | 9/1992 | Euteneuer et al. | |
| 5,152,773 A | 10/1992 | Redha | |
| 5,156,594 A | 10/1992 | Keith | |
| 5,156,610 A | 10/1992 | Reger | |
| 5,158,564 A | 10/1992 | Schnepp-Pesch et al. | |
| 5,176,693 A | 1/1993 | Pannek, Jr. | |
| 5,178,625 A | 1/1993 | Groshong | |
| 5,180,368 A | 1/1993 | Garrison | |
| 5,192,291 A | 3/1993 | Pannek, Jr. | |
| 5,196,024 A * | 3/1993 | Barath | 606/159 |
| 5,196,025 A | 3/1993 | Ranalletta et al. | |
| 5,209,749 A | 5/1993 | Buelna | |
| 5,209,799 A | 5/1993 | Vigil | |
| 5,224,945 A | 7/1993 | Pannek, Jr. | |
| 5,226,430 A | 7/1993 | Spears et al. | |
| 5,226,887 A | 7/1993 | Farr et al. | |
| 5,226,909 A | 7/1993 | Evans et al. | |
| 5,242,396 A | 9/1993 | Evard | |
| 5,248,311 A | 9/1993 | Black et al. | |
| 5,250,059 A | 10/1993 | Andreas et al. | |
| 5,295,959 A | 3/1994 | Gurbel et al. | |
| 5,300,025 A | 4/1994 | Wantink | |
| 5,312,425 A | 5/1994 | Evans et al. | |
| 5,318,576 A | 6/1994 | Plassche, Jr. et al. | |
| 5,320,634 A * | 6/1994 | Vigil et al. | 606/159 |
| 5,328,472 A | 7/1994 | Steinke et al. | |
| 5,336,234 A | 8/1994 | Vigil et al. | |
| 5,342,301 A | 8/1994 | Saab | |
| 5,342,307 A | 8/1994 | Euteneuer et al. | |
| 5,346,505 A | 9/1994 | Leopold | |
| 5,350,361 A * | 9/1994 | Tsukashima et al. | 604/103.07 |
| 5,372,601 A | 12/1994 | Lary | |
| 5,395,361 A | 3/1995 | Fox et al. | |
| 5,399,164 A | 3/1995 | Snoke et al. | |
| 5,403,334 A | 4/1995 | Evans et al. | |
| 5,409,454 A | 4/1995 | Fischell et al. | |
| 5,411,466 A | 5/1995 | Hess | |
| 5,411,478 A | 5/1995 | Stillabower | |
| 5,415,654 A | 5/1995 | Daikuzono | |
| 5,417,653 A | 5/1995 | Sahota et al. | |
| 5,417,703 A | 5/1995 | Brown et al. | |
| 5,423,745 A | 6/1995 | Todd et al. | |
| 5,425,711 A | 6/1995 | Ressemann et al. | |
| 5,425,712 A | 6/1995 | Goodin | |
| 5,437,659 A | 8/1995 | Leckrone | |
| 5,441,510 A | 8/1995 | Simpson et al. | |
| 5,449,343 A | 9/1995 | Samson et al. | |
| 5,456,666 A | 10/1995 | Campbell et al. | |
| 5,456,681 A | 10/1995 | Hajjar | |
| 5,458,572 A | 10/1995 | Campbell et al. | |
| 5,478,319 A | 12/1995 | Campbell et al. | |
| 5,487,730 A | 1/1996 | Marcadis et al. | |
| 5,496,308 A | 3/1996 | Brown et al. | |
| 5,507,760 A | 4/1996 | Wynne et al. | |
| 5,507,761 A | 4/1996 | Duer | |
| 5,522,818 A | 6/1996 | Keith et al. | |
| 5,522,825 A | 6/1996 | Kropf et al. | |
| 5,538,510 A | 7/1996 | Fontirroche et al. | |
| 5,549,556 A | 8/1996 | Ndondo-Lay et al. | |
| 5,554,121 A | 9/1996 | Ainsworth et al. | |
| 5,556,405 A | 9/1996 | Lary | |
| 5,556,408 A | 9/1996 | Farhat | |
| 5,569,277 A | 10/1996 | Evans et al. | |
| 5,571,087 A | 11/1996 | Ressemann et al. | |
| 5,616,149 A | 4/1997 | Barath | |
| 5,628,761 A | 5/1997 | Rizik | |
| 5,643,209 A | 7/1997 | Fugoso et al. | |
| 5,643,278 A * | 7/1997 | Wijay | 623/1.11 |
| 5,643,296 A | 7/1997 | Hundertmark et al. | |
| 5,649,941 A | 7/1997 | Lary | |
| 5,662,671 A | 9/1997 | Barbut et al. | |
| 5,669,920 A | 9/1997 | Conley et al. | |
| 5,681,336 A | 10/1997 | Clement et al. | |
| 5,697,944 A | 12/1997 | Lary | |
| 5,713,913 A | 2/1998 | Lary et al. | |
| 5,718,684 A | 2/1998 | Gupta | |
| 5,720,724 A | 2/1998 | Ressemann et al. | |
| 5,728,123 A | 3/1998 | Lemelson et al. | |
| 5,730,698 A * | 3/1998 | Fischell et al. | 600/3 |
| 5,743,875 A | 4/1998 | Sirhan et al. | |
| 5,759,191 A | 6/1998 | Barbere | |
| 5,769,819 A | 6/1998 | Schwab et al. | |
| 5,769,865 A | 6/1998 | Kermode et al. | |
| 5,792,158 A | 8/1998 | Lary | |
| 5,797,935 A | 8/1998 | Barath | |
| 5,800,450 A | 9/1998 | Lary et al. | |
| 5,820,594 A | 10/1998 | Fontirroche et al. | |
| 5,824,173 A | 10/1998 | Fontirroche et al. | |
| 5,827,201 A | 10/1998 | Samson et al. | |
| 5,827,225 A | 10/1998 | Ma Schwab | |
| 5,827,310 A | 10/1998 | Mann et al. | |
| 5,895,402 A | 4/1999 | Hundertmark et al. | |
| 5,921,958 A | 7/1999 | Ressemann et al. | |
| 5,931,819 A | 8/1999 | Fariabi | |
| 5,993,469 A | 11/1999 | McKenzie et al. | |

| | | |
|---|---|---|
| 5,997,557 A | 12/1999 | Barbut et al. |
| 6,010,521 A | 1/2000 | Lee et al. |
| 6,024,722 A | 2/2000 | Rau et al. |
| 6,030,371 A | 2/2000 | Pursley |
| 6,039,699 A | 3/2000 | Viera |
| 6,066,149 A | 5/2000 | Samson et al. |
| 6,068,623 A | 5/2000 | Zadno-Azizi et al. |
| 6,099,518 A * | 8/2000 | Adams et al. ............... 604/523 |
| 6,110,192 A | 8/2000 | Ravenscroft et al. |
| 6,117,153 A | 9/2000 | Lary et al. |
| 6,139,510 A | 10/2000 | Palermo |
| 6,142,975 A | 11/2000 | Jalisi et al. |
| 6,165,140 A | 12/2000 | Ferrera |
| 6,165,167 A | 12/2000 | Delaloye |
| 6,165,292 A | 12/2000 | Abrams et al. |
| 6,168,571 B1 | 1/2001 | Solar et al. |
| 6,179,851 B1 | 1/2001 | Barbut et al. |
| 6,190,332 B1 | 2/2001 | Muni et al. |
| 6,193,686 B1 | 2/2001 | Estrada et al. |
| 6,213,957 B1 | 4/2001 | Milliman et al. |
| 6,217,549 B1 | 4/2001 | Selmon et al. |
| 6,217,567 B1 | 4/2001 | Zadno-Azizi et al. |
| 6,221,006 B1 | 4/2001 | Dubrul et al. |
| 6,241,690 B1 | 6/2001 | Burkett et al. |
| 6,254,550 B1 | 7/2001 | McNamara et al. |
| 6,258,108 B1 | 7/2001 | Lary |
| 6,283,743 B1 | 9/2001 | Traxler et al. |
| 6,306,105 B1 | 10/2001 | Rooney et al. |
| 6,306,151 B1 * | 10/2001 | Lary ........................... 606/159 |
| 6,309,399 B1 | 10/2001 | Barbut et al. |
| 6,344,029 B1 | 2/2002 | Estrada et al. |
| 6,355,016 B1 | 3/2002 | Bagaoisan et al. |
| 6,383,146 B1 | 5/2002 | Klint |
| 6,387,075 B1 | 5/2002 | Stivland et al. |
| 6,394,995 B1 | 5/2002 | Solar et al. |
| 6,398,798 B2 | 6/2002 | Selmon et al. |
| 6,409,863 B1 | 6/2002 | Williams et al. |
| 6,425,882 B1 * | 7/2002 | Vigil ....................... 604/99.01 |
| 6,471,673 B1 | 10/2002 | Kastenhofer |
| 6,471,713 B1 | 10/2002 | Vargas et al. |
| 6,533,754 B1 | 3/2003 | Hisamatsu et al. |
| 6,544,276 B1 | 4/2003 | Azizi |
| 6,562,062 B2 | 5/2003 | Jenusaitis et al. |
| 6,602,265 B2 | 8/2003 | Dubrul et al. |
| 6,632,231 B2 * | 10/2003 | Radisch, Jr. ................. 606/159 |
| 2002/0010489 A1 * | 1/2002 | Grayzel et al. ............. 606/194 |
| 2003/0163148 A1 * | 8/2003 | Wang et al. ................. 606/159 |

FOREIGN PATENT DOCUMENTS

| | | |
|---|---|---|
| DE | 3402573 | 8/1985 |
| DE | 35 19 626 A1 | 12/1986 |
| EP | 0 291 170 A1 | 11/1988 |
| EP | 0 414 350 A1 | 2/1991 |
| EP | 0 784 966 B1 | 7/1997 |
| EP | 0 792 656 A1 | 9/1997 |
| GB | 1 547 328 | 6/1979 |
| WO | WO 90/07909 A1 | 7/1990 |
| WO | WO 91/17714 A1 | 11/1991 |

OTHER PUBLICATIONS

Lary, Banning G., "A Method to Create and Correct Stenosis of a Coronary Artery," *Archives of Surgery*, Nov. 1966, vol. 93, pp. 828-830.

Lary, Banning G., "An Epicaridal Purse String Suture for Closing Coronary Arteriotomy," *The American Surgeon*, Mar. 1967, vol. 33, No. 3, pp. 213-214.

Lary, Banning G., "Coronary Artery Incision and Dilation," *Archives of Surgery*, Dec. 1980, vol. 115, pp. 1478-1480.

Lary, Banning G., "Coronary Artery Resection and Replacement by a Blood Conduit," *Surgery*, Apr. 1969, vol. 65, No. 4, pp. 584-589.

Lary, Banning G., "Effect of Endocardial Incisions on Myocardial Blood Flow," *Archives of Surgery*, Sep. 1963, vol. 87, pp. 424-427.

Lary, B.G., "Experimental Maintenance of Life by Intravenous Oxygen, Preliminary Report," *Clinical Congress of the American College of Surgeons*, San Francisco, Nov. 5-9, 1951, pp. 30-35.

Lary, Banning G., et al., "Experimental Vein Angioplasty of the Circumflex Coronary Artery," *Journal of Surgical Research*, Sep. 1974, vol. 17, No. 3, pp. 210-214.

Lary, Banning G., "Method for Increasing the Diameter of Long Segments of the Coronary Artery," *The American Surgeon*, Jan. 1966, vol. 32 No. 1, 33-35.

Lary, Banning G., et al., "Myocardial Revascularization Experiments Using the Epicardium," *Archives of Surgery*, Jan. 1969, vol. 98, pp. 69-72.

Lary, Banning G., "Onlay Vein Graft for the Correction of Coronary Artery Obstruction," *Surgery*, Apr. 1966, vol. 59, No. 4, pp. 547-551.

Lary, Banning G., "Surgery for Coronary Artery Disease," *Nursing Clinics of North America*, Sep. 1967, vol. 2, No. 3, pp. 537-542.

Lary, Banning G., et al., "The 'Coronary Myocardial Artery' for Coronary Artery Disease," *Diseases of the Chest*, Apr. 1996, vol. 49, No. 4, pp. 412-419.

* cited by examiner

CUTTING BALLOON CATHETER WITH IMPROVED BALLOON CONFIGURATION

FIELD OF THE INVENTION

The present invention pertains to angioplasty and angioplasty balloon catheters. More particularly, the present invention pertains to angioplasty balloon catheters that include one or more cutting edges and angioplasty balloons with improved folding and re-folding properties.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated, and the restriction of the vessel is opened.

One of the major obstacles in treating coronary artery disease and/or treating blocked blood vessels is re-stenosis. Evidence has shown that cutting the stenosis, for example with an angioplasty balloon equipped with a cutting blade, during treatment can reduce incidence of re-stenosis. Additionally, cutting the stenosis may reduce trauma at the treatment site and/or may reduce the trauma to adjacent healthy tissue. Cutting blades may also be beneficial additions to angioplasty procedures when the targeted occlusion is hardened or calcified. It is believed typical angioplasty balloons, alone, may not be able to expand certain of these hardened lesions. Thus, angioplasty balloons equipped with cutting edges have been developed to attempt to enhance angioplasty treatments. There is an ongoing need for improved angioplasty devices, including cutting angioplasty balloons, and improved methods of treating intravascular stenoses and occlusions.

Another potential obstacle that may accompany treatments that include expansion of a stenosis with an angioplasty balloon is the removal of the balloon from the vessel. This is because when the balloon is deflated, it may tend to maintain a relatively large profile. Moreover, if the balloon includes a cutting edge, the potential exists for the cutting edge to be disposed at a large profile region of the balloon. This could subject healthy tissue to unnecessary contact with the cutting edge and resultant abrasion or cutting during the balloon removal procedure. Accordingly, there is an ongoing need for improved angioplasty devices, including cutting angioplasty balloons, with improved re-folding abilities.

BRIEF SUMMARY

The present invention relates to angioplasty balloon catheters. In at least some embodiments, an example balloon catheter may include a catheter shaft having a balloon coupled thereto. The balloon may include one or more cutting members or blades. Additionally, the balloon may include a number of wings when the balloon is deflated or partially deflated. The wings may improve the folding and refolding abilities of the balloon. The wings may also include one or more undulating surfaces. These and other features are described in more detail below.

DETAILED DESCRIPTION

Figure 1:
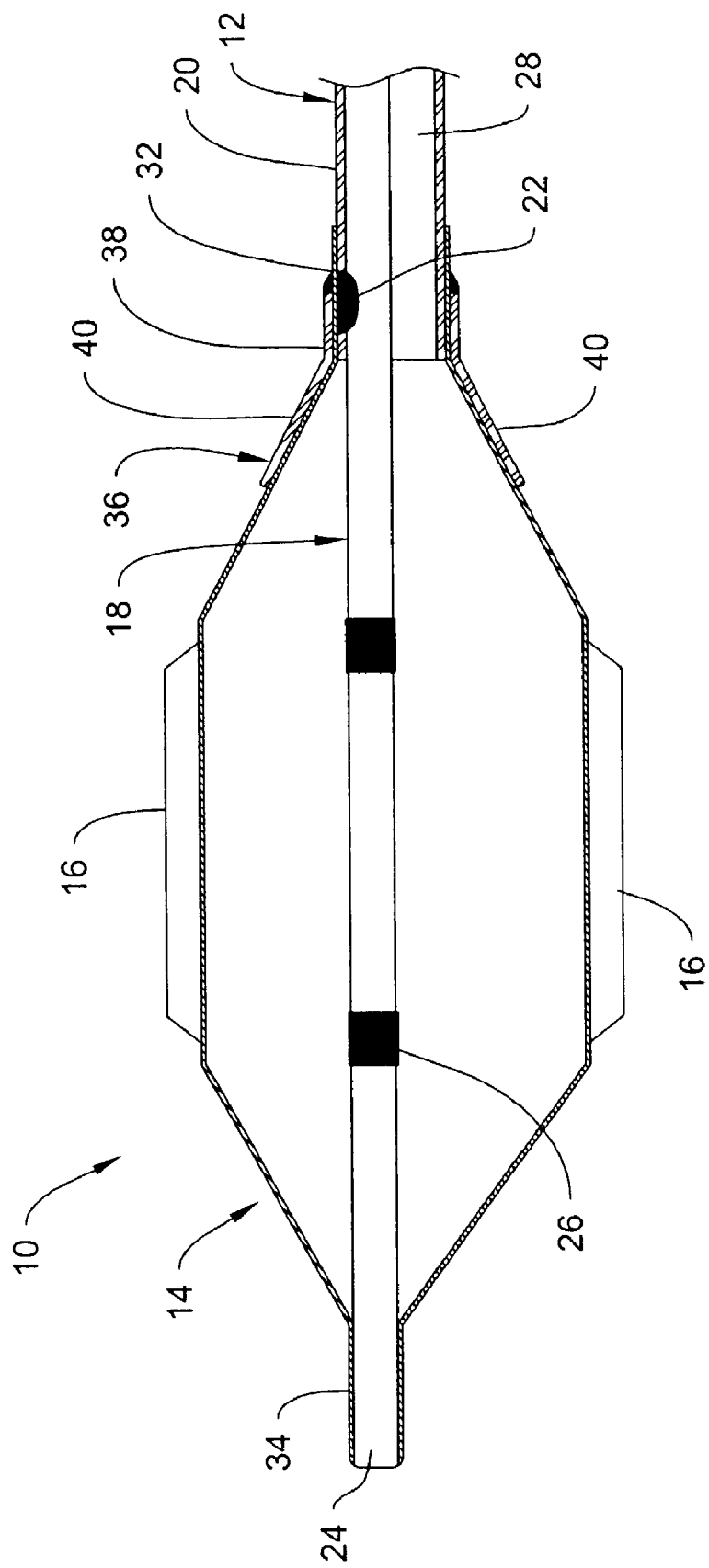
FIG. 1 is a partial cross-sectional side view of a distal portion of a balloon catheter.

The following description should be read with reference to the drawings wherein like reference numerals indicate like elements throughout the several views. The detailed description and drawings illustrate example embodiments of the claimed invention.

FIG. 1 is a partial cross-sectional side view of a distal portion of a catheter 10. Catheter 10 includes a catheter shaft 12 and an expandable balloon 14 coupled to shaft 12. Balloon 14 may include one or more cutting members 16 that may be used, for example, to sever tissue adjacent a stenosis and/or otherwise compliment the expansion of a stenotic lesion. In general, balloon catheter 10 may include similarities in structure and use to other balloon catheters. For example, catheter 10 can be advanced through the vasculature to a position adjacent a target area (e.g., an intravascular lesion) and balloon 14 may be expanded to expand the lesion. Uses for catheter 10 may include cardiac interventions as well as peripheral interventions including esophageal, urethral, and other peripheral interventions.

In at least some embodiments, balloon 14 may be configured to have desirable folding and re-folding abilities. For example, balloon 14 may be adapted to have "wings" (best seen in FIGS. 2 and 3) that are pre-formed during manufacturing and that can be seen when balloon 14 is deflated. The wings allow balloon 14 to re-fold into a relatively low-profile configuration so that balloon 14 can be more easily removed from the blood vessel. Additionally, the wings may be able to roll over or otherwise fold over and cover cutting members 16 so as to shield the vessel from cutting members 16 during the transportation of balloon 14. Some of the other features and benefits of catheter 10 are described in more detail below.

Cutting members 16 may be a blade or other structure configured for cutting into tissue such as a lesion. For example, cutting members 16 may include a metallic cutting blade that is similar to a knife. However, the material composition, shape, and appearance of cutting members 16 may vary. Cutting members 16 may be attached to balloon 14 in any suitable way. For example, cutting members 16 may be secured by adhesives. Alternatively, cutting members 16 may be connected to balloon 14 using welding (e.g., resistance or laser welding), soldering, brazing, thermal bonding, or the like, combinations thereof, or any suitable method.

In some embodiments, four cutting members 16 are disposed around balloon 14. However, the exact number of cutting members 16 and the exact position of cutting members 16 on balloon 14 may vary. For example, balloon 14 may include one to six cutting members 16 or more and the cutting members 16 may be regularly distributed, irregularly distributed, randomly distributed, or otherwise disposed in any manner.

Balloon 14 may be made from typical angioplasty balloon materials including polymers such as polyethylene terephthalate (PET), polyetherimid (PEI), polyethylene (PE), etc. Some other examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro (propyl vinyl ether) (PFA), other suitable materials, or mixtures, combinations, copolymers thereof, polymer/metal composites, and the like. Alternatively, balloon 14 may be made from other materials including those which may be somewhat stronger or stiffer in order to provide structural support for cutting members 16. Accordingly, the stiffer materials may be disposed adjacent cutting members 16. Some examples of these stiffer materials include polymers blended with liquid crystal polymer (LCP) as well as the materials listed above. For example, the mixture can contain up to about 5% LCP.

Catheter shaft 12 may include an inner tubular member 18 and an outer tubular member 20. Tubular members 18/20 may be manufactured from a number of different materials. For example, tubular members 18/20 may be made of metals, metal alloys, polymers, metal-polymer composites, or any other suitable materials. Some examples of suitable metals and metal alloys include stainless steel, such as 304V, 304L, and 316L stainless steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material. Some examples of suitable polymers include those described above in relation to balloon 14.

Tubular members 18/20 may be arranged in any appropriate way. For example, in some embodiments inner tubular member 18 can be disposed coaxially within outer tubular member 20. According to these embodiments, inner and outer tubular members 18/20 may or may not be secured to one another along the general longitudinal axis of catheter shaft 12. Alternatively, inner tubular member 18 may follow the inner wall or otherwise be disposed adjacent the inner wall of outer tubular member 20. Again, inner and outer tubular members 18/20 may or may not be secured to one another. For example in one preferred embodiment, inner and outer tubular members 20 may be bonded, welded (including tack welding or any other welding technique), or otherwise secured at a bond point 22. In some embodiments, bond point 22 may be generally disposed near the distal end of catheter shaft 12. However, one or more bond points 22 may be disposed at any position along shaft 12. Bond 22 may desirably impact, for example, the stability and the ability of tubular members 18/20 to maintain their position relative to one another. In still other embodiments, inner and outer tubular member 18/20 may be substantially parallel to one another so that they are non-overlapping. In these embodiments, shaft 12 may include an outer sheath that is disposed over tubular members 18/20.

Inner tubular member 18 may include an inner lumen 24. In at least some embodiments, inner lumen 24 is a guidewire lumen. Accordingly, catheter 10 can be advanced over a guidewire to the desired location. The guidewire lumen may extend along essentially the entire length of catheter shaft 12 so that catheter 10 resembles traditional "over-the-wire" catheters. Alternatively, the guidewire lumen may extend along only a portion of shaft 12 so that catheter 10 resembles "single-operator-exchange" or "rapid-exchange" catheters.

In some embodiments, one or more marker members 26 may be coupled to inner tubular member 18, or at essentially any other suitable position on catheter 10. Marker members 26 may include, be made from, be doped with, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, plastic material loaded with a radiopaque filler, and the like.

Shaft 12 may also include an inflation lumen 28 that may be used, for example, to transport inflation media to and from balloon 14. The location and position of inflation lumen 28 may vary, depending on the configuration of tubular members 18/20. For example, when outer tubular member 20 is disposed over inner tubular member 18, inflation lumen 28 may be defined within the annular space between tubular members 18/20. Moreover, depending on the position of inner tubular member 18 within outer tubular member 20, the shape of lumen 28 may vary. For example, if inner tubular member 18 is attached to or disposed adjacent to the inside surface of outer tubular member 20, then inflation lumen 28 may be generally half-moon in shape; whereas if inner tubular member 18 is generally coaxial with outer tubular member 20, then inflation lumen 28 may be generally ring-shaped or annular in shape. It can be appreciated that if outer tubular member 20 is disposed alongside inner tubular member 18, then lumen 28 may be the lumen of outer tubular member 20 or it may be the space defined between the outer surface of tubular members 18/20 and the outer sheath disposed thereover.

Balloon 14 may be coupled to catheter shaft 12 in any of a number of suitable ways. For example, balloon 14 may be adhesively or thermally bonded to shaft 12. In some embodiments, a proximal portion 32 of balloon 14 may be bonded to shaft 12, for example, at outer tubular member 20, and a distal portion 32 may be bonded to shaft 12, for example, at inner tubular member 18. The exact bonding positions, however, may vary.

A folding spring 36 may be coupled to balloon 14, for example, adjacent proximal portion 32. A description of a suitable folding spring, essentially the same in form and function as folding spring 36, can be found in U.S. Pat. No.

6,425,882 the disclosure, of which is incorporated herein by reference. Folding spring 36 may generally include a base or band 38 and one or more fingers 40 extending distally from base 38. Fingers 40 may be adapted to shift between a first collapsed configuration and a second expanded configuration. In some embodiments, fingers 40 are biased to be in the first configuration. Accordingly, when balloon 14 is collapsed, fingers 40 assume the first configuration and when balloon 14 is expanded, the outward force of balloon 14 on fingers 40 can overcome the bias so that fingers 40 assume the second configuration. The ability of folding spring 36 to shift between configurations may assist balloon refolding or otherwise improve the refolding ability of balloon 14. For example, biasing folding spring 36 in the first configuration may allow fingers 40 to exert force on balloon 14 (when not inflated) so that balloon 14 may be at least partially collapsed.

Figure 2:
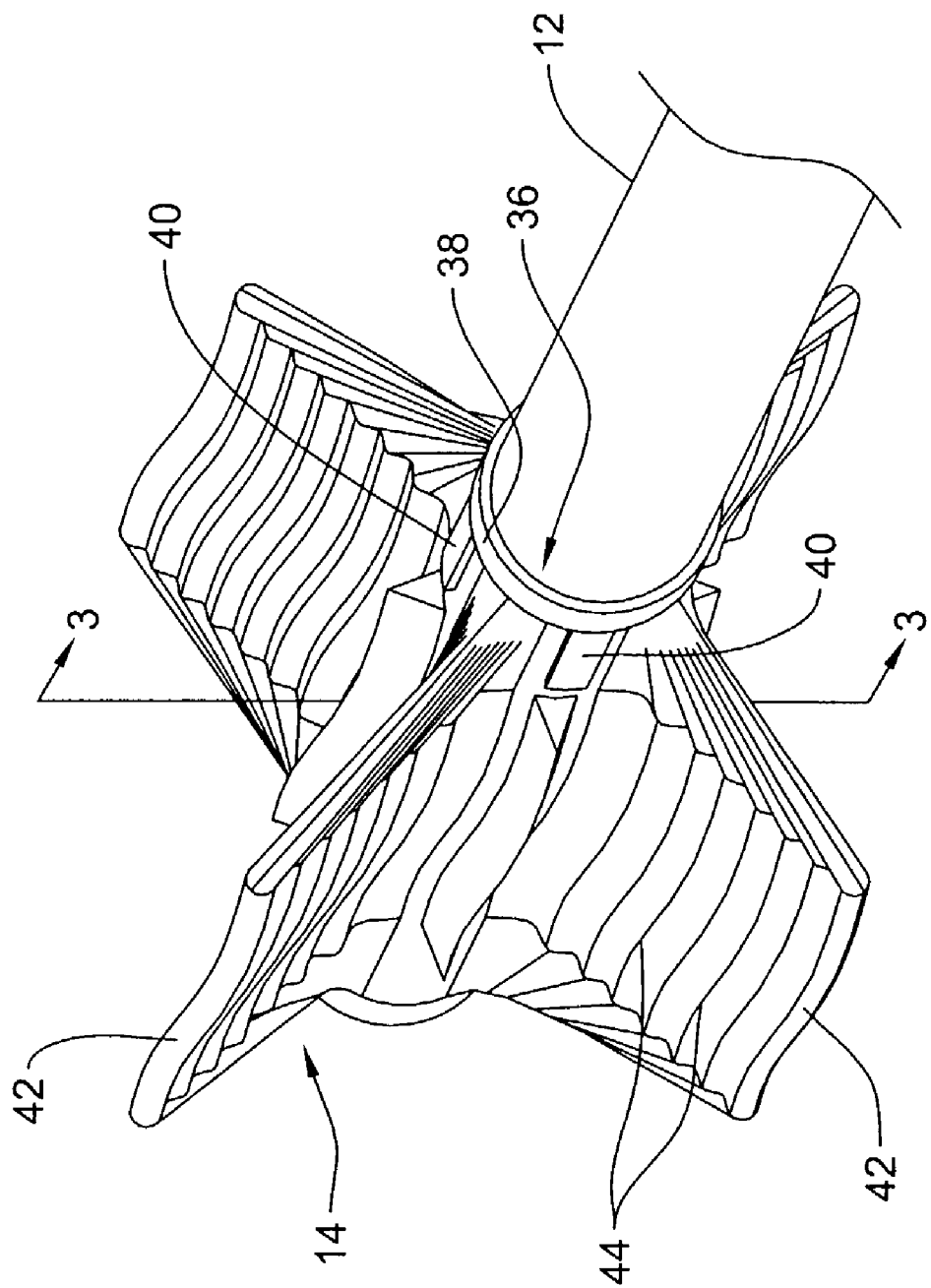
FIG. 2 is a perspective view of a balloon catheter that is deflated to illustrate a plurality of wings in the balloon.

Balloon 14 may be configured so that it includes one or more wings 42 as shown in FIG. 2. In general, wings 42 are visible and can be seen when balloon 14 is deflated. The appearance of wings 42 includes a plurality of alternating inward and outward radial deflection in balloon 14. Wings 42 may allow balloon 14 to have more predictable and consistent re-folding characteristics. For example, wings 42 may help balloon 14 fold inward at a plurality of positions so that the overall profile of balloon 14 in a deflated state can be reduced. In some embodiments, balloon 14 includes four wings 42. However, the number of wings 42 can vary and can be any suitable number such as three, five, six, or more. The distribution of wings 42 may also vary. For example, wings 42 may be evenly, regularly, irregularly, randomly, or otherwise dispersed in any manner about balloon 14.

In at least some embodiments, wings 42 may be dispersed so that wings 42 and cutting members 16 alternate. Additionally, it may be desirable to configure wings 42 so that cutting members 16 are positioned at the inward-most positions of wings 42. This arrangement allows cutting members 16 to be positioned more closely to shaft 12 when balloon 14 is deflated. Accordingly, cutting members 16 can be moved away from the vessel walls where they might otherwise result in contact and, possibly, damage to healthy tissue during movement of catheter 10 within a body lumen. Additionally, alternating wings 42 and cutting members 12 as well as positioning cutting members 16 relatively close to shaft 12 may allow wings 42 to fold over and cover cutting members 16 when balloon 14 is deflated. Again, this feature may reduce the exposure of cutting members 16 to the blood vessel.

Wings 42 may also include one or more undulations or an undulating surface as indicated in FIG. 2 by reference number 44. In general, undulations 44 may resemble waves or peaks and valleys formed in wings 42. In some embodiments, the "peaks" of undulations 44 line up along the longitudinal axis of balloon 14. However, this need not be the case. Additionally, the number, arrangements, and position of undulations 44 may vary in different example embodiments as well as among the different wings 42 of a particular embodiment. For example, some example wings 42 may include relatively few undulations 44 while other example wings 42 may include several. Moreover, some wing 42 embodiments may include undulations 44 that have opposing "peaks" similar to what is shown in FIG. 3, while other wings 42 may include nesting or aligned peaks or any other suitable configuration.

Undulations 44 may be desirable for a number of reasons. For example, undulations 44 may increase the surface area of wings 42 so that wings 42 have a shorter radial length than they would otherwise have without undulations 44. Accordingly, when balloon 14 is in the deflated configuration, undulations 44 may allow wings 42 to be even closer to shaft 12 and, thus, decrease the overall profile of deflated balloon 14.

Also shown in FIG. 2 is that folding spring 36 may be configured so that fingers 40 can extend between adjacent wings 42. Because folding spring 36 may be biased to be in the collapsed configuration (as described above), fingers 40 may help balloon 14 collapse and expose wings 42 by exerting force on balloon 14 between wings 42. The bias of folding spring 36 may be overcome by infusing inflation media into balloon 14 and inflating balloon 14.

Figure 3:
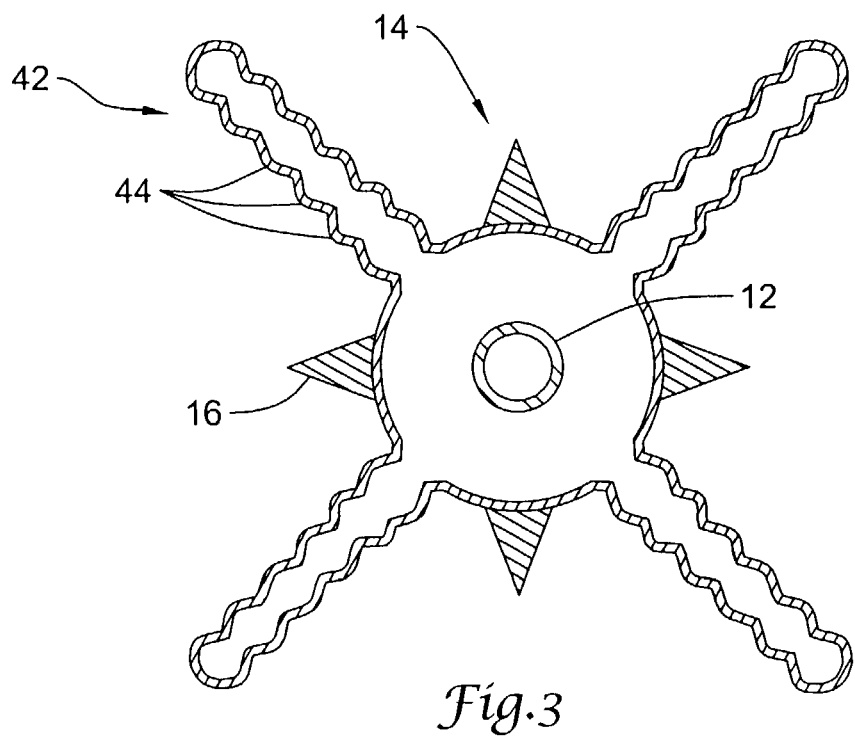
FIG. 3 is a cross-sectional view taken along line 3-3 in FIG. 2.

FIG. 3 is a cross-sectional view taken along line 3-3 in FIG. 2 that shows undulations 44 disposed in wings 42. Here it can be seen how undulations 44 may define waves with longitudinally-aligned peaks and valleys. Of course, other embodiments may include waves with differing configurations such as non-aligned waves. It can also be seen how the peaks of undulations 44 may be opposed. Alternative embodiments, however, include undulations 44 that are nested or aligned, randomly distributed, or include various combinations of configurations. Also shown in FIG. 3 is a portion of shaft 12, for example inner tubular member 18, extending at least partially through balloon 14.

Figure 4:
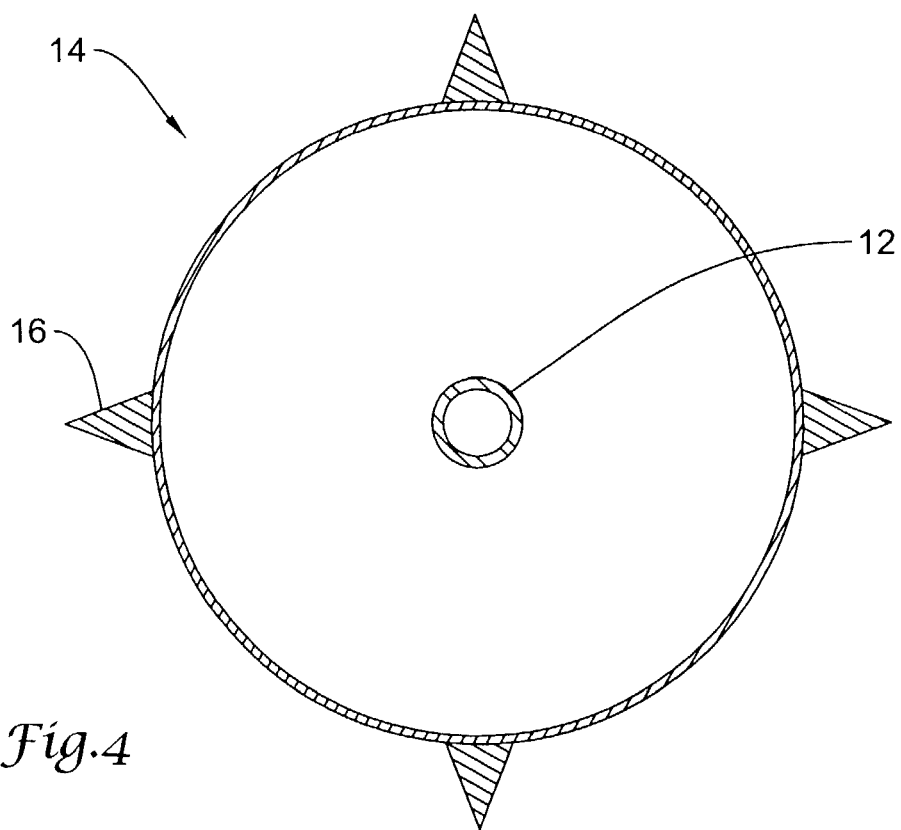
FIG. 4 is an alternative cross-sectional view of the balloon when inflated.

When balloon 14 is inflated, wings 42 may become expanded and, thus, not visible as illustrated in FIG. 4. This alternative cross-sectional view shows how inflating balloon 14 can essentially expand wings 42 and move cutting members 16 toward the outer periphery of balloon 14 for the desired cutting action. It can be appreciated that upon deflation, balloon 14 can assume the winged configuration shown in FIG. 3.

Figure 5:
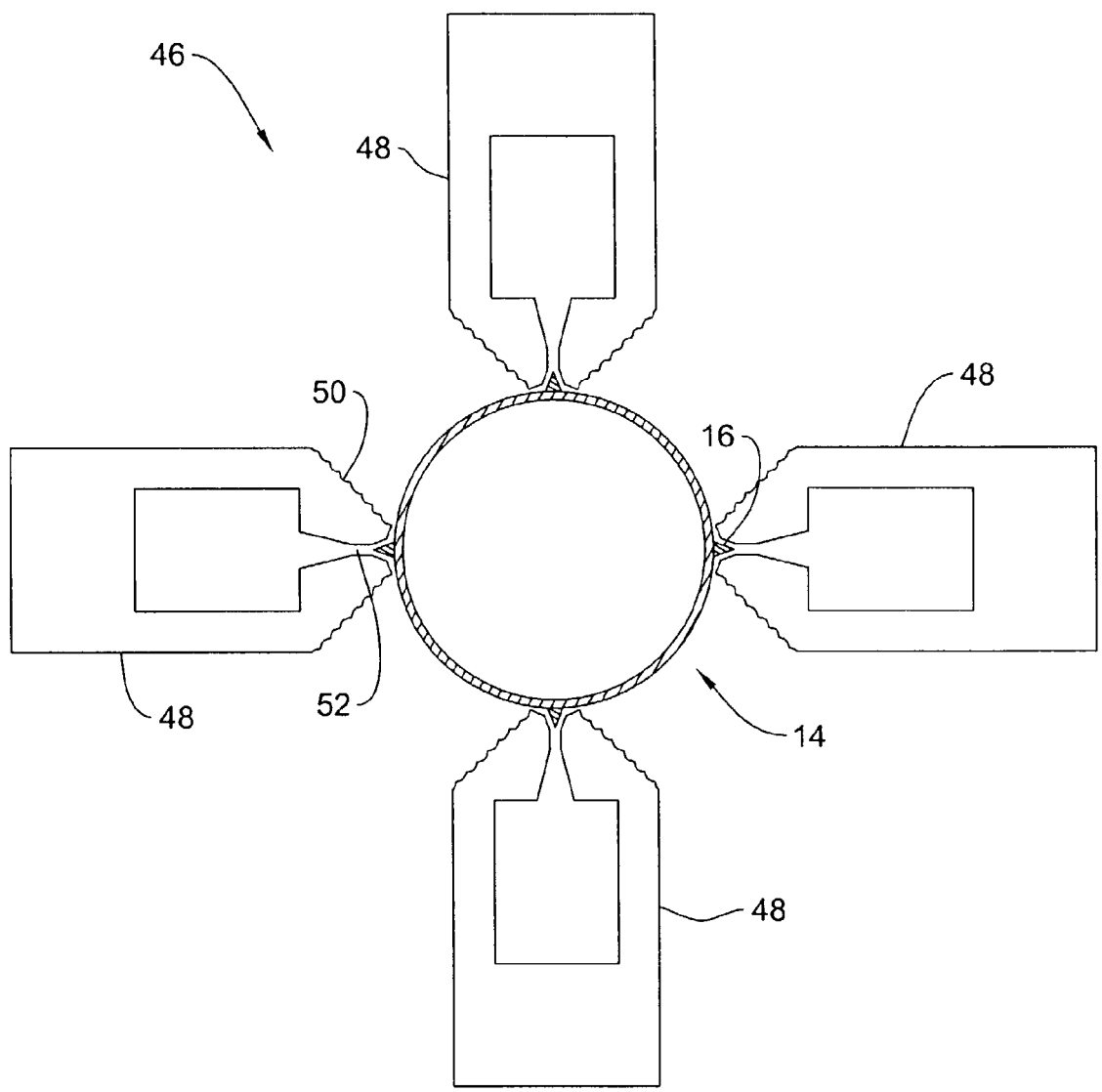
FIG. 5 is a schematic view of a wing-forming device and a balloon disposed therein prior to wing formation.

FIG. 5 is a schematic view of a wing-forming apparatus 46 that may be used to form wings 42 and/or undulations 44. Wing-forming apparatus 46 may include a plurality of jaws or jaw members 48 that each include an undulating surface 50 and a blade opening 52. Jaw members 48 may be generally metallic and can be used to "iron" or otherwise define wings 42 and undulations 44 in wings 42. The ironing process may include aligning balloon 14 and jaw members 48 so that cutting members 16 are disposed adjacent blade openings 52. In some embodiments, jaw members 48 may be movably mounted to a frame structure so that jaw members 48 can be moved inwardly toward the center of balloon 14. The result may be balloon 14 bending inward similar to what is shown in FIG. 6.

In at least some embodiments, the use of apparatus 46 may include subjecting balloon 14 to heat and/or pressure in order to form and define wings 42 and undulations 44 in balloon 14. Generally, wings 42 can be defined in balloon 14 adjacent spaces between a pair of jaw members 48 and undulations 44 may be defined adjacent undulating surfaces 50 of jaw members 48. The source of the heat and pressure may vary. For example, apparatus 46 may be disposed within an oven or other suitable heating device so that the balloon can be heated during the ironing procedure. Additionally, the oven may also include pressure controls so that the pressure within the oven may be varied. Alternatively, heat and pressure may be provided by other sources such as external electrodes or connectors, electrical or other types of energy, or in any other suitable manner. Generally, the use of apparatus 46 results in the alteration of the geometry of balloon 14 so that a generally repeatable deflation shape is formed in the balloon material so that wings 42 are formed and visible when balloon 14 is deflated. It is believed that the disclosed balloon geometry, that may include a plurality of wings 42 having undulations 44, helps render the balloon more foldable, more re-foldable, and more collapsible.

Figure 6:
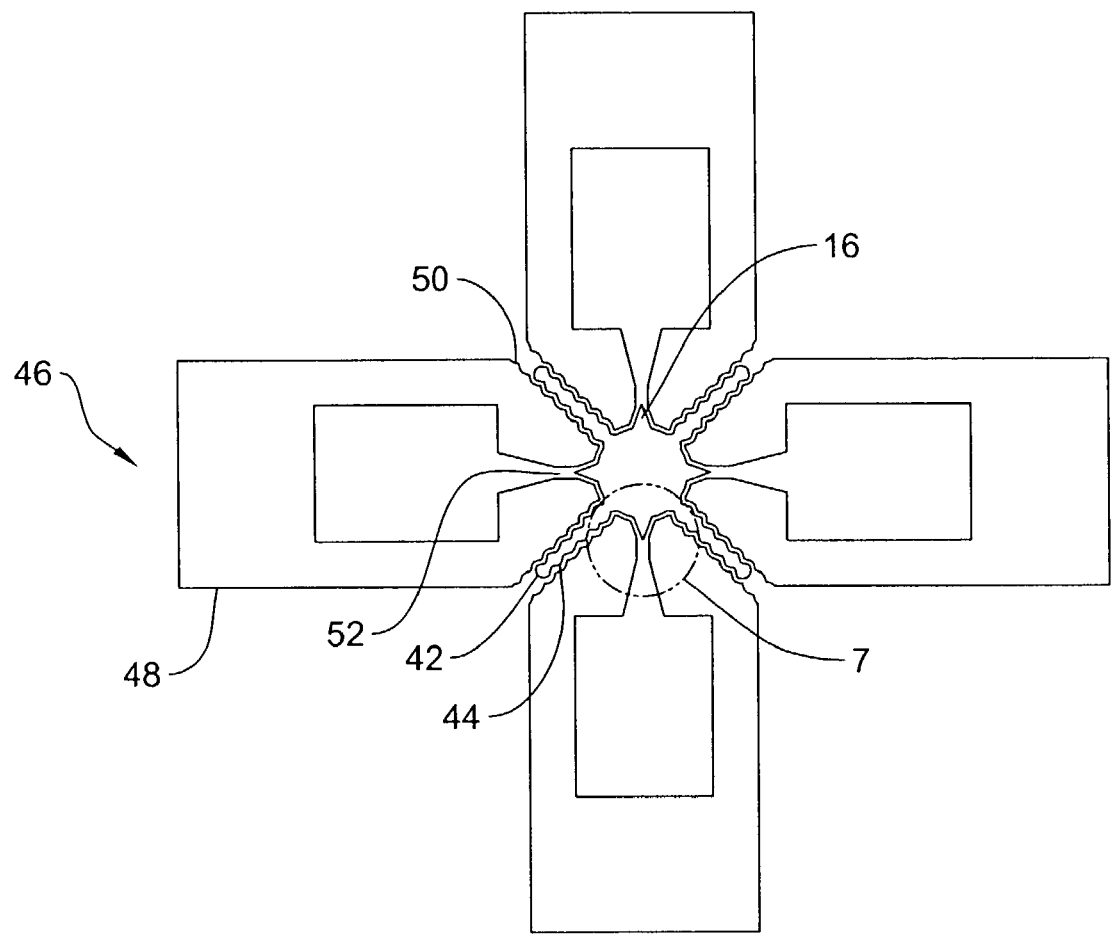
FIG. 6 is a schematic view of the wing-forming device and balloon of FIG. 5 where the jaws of the wing-forming device are closed.

Apparatus 46 may alternatively be configured similarly to what is shown in FIG. 6 so that balloon 14 may be aligned with jaw members 48 (e.g., with cutting members 16 aligned with blade openings 52) and pushed, pulled, or otherwise advanced into contact with and/or through apparatus 46. This arrangement allows wings 42 to be formed and undulations 44 to be defined by undulating surfaces 50.

Figure 7:
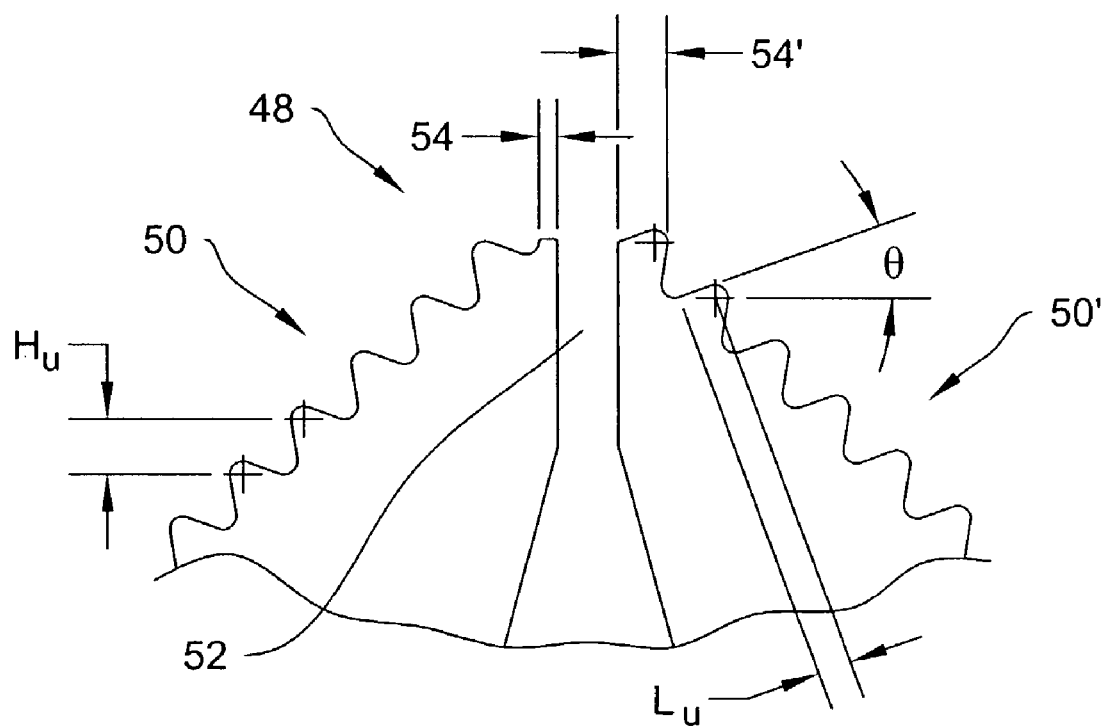
FIG. 7 is an enlarged view of a jaw member.

FIG. 7 is an enlarged view of jaw member 48 that illustrates some example configurations and dimensions. First, it can be seen that jaw member 48 can have a pair of undulating surfaces 50/50'. In some embodiments, surfaces 50/50' may be substantially symmetrical. Alternatively, surfaces 50/50' may be somewhat offset from one another. For example, surface 50 may have a relatively short top undulation portion 54 that may be about 0.002 to about 0.012 inches long, and surface 50' may have a somewhat longer top undulation portion 54' that may be about 0.012 to about 0.028 inches long. Staggering or offsetting top portions 54/54' may be desirable, for example, by allowing for adjacent jaw members 48 to be disposed more closely to one another by positioning a short top portion (e.g., similar to portion 54) adjacent a somewhat longer top portion (e.g., similar to portion 54').

FIG. 7 also illustrates that undulating surfaces 50/50' may be sized to define undulations 44 having an undulation height, $H_U$, and an undulation length, $L_U$. The precise dimension for $H_U$ and $L_U$ may vary. For example, $H_U$ and $L_U$ may each be about 0.010 to about 0.030 inches or so. In some embodiments, $H_U$ and $L_U$ may be the same size as one another, while in other embodiments they may differ. Similarly, opposing undulating surfaces 50/50' may have undulations with the same or different $H_U$ and $L_U$. Undulating surfaces 50/50' may also rise adjacent an individual undulation at an angle θ that may be about 5 to about 15 degree or so. Angle θ may be the same or different among individual undulations of a particular surface (e.g., surface 50 or 50') and, similarly, may vary between different undulating surfaces 50/50'.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An angioplasty balloon catheter, comprising:
   an elongate catheter shaft;
   an expandable balloon coupled to the shaft, the balloon including a length and being configured to shift between a first generally deflated configuration prior to use, a generally inflated configuration, and a second generally deflated configuration, the balloon including an outer surface;
   wherein the balloon includes a plurality of wings formed therein when the balloon is in the deflated configuration;
   the wings each including a wing tip and a pair of undulating side surfaces that extend along substantially the entire length of the balloon, wherein at least one of the undulating side surfaces has a plurality of smooth and rounded undulations defined therein that are disposed in a regular pattern, where each of the undulations includes at least one peak and at least one valley;
   wherein at least one of the wings includes peaks and valleys on one of the undulating side surfaces that are longitudinally-aligned with the peaks and valleys on the other undulating side surface;
   wherein the balloon includes the undulations when the balloon is in the second generally deflated configuration; and
   a plurality of cutting members coupled to the outer surface of the balloon, wherein each of the cutting members is disposed on the outer surface of the balloon at a position between a pair of adjacent wings.

2. The catheter of claim 1, further comprising a folding spring coupled to the balloon.

3. A cutting balloon angioplasty device, comprising:
   an elongate shaft having a proximal end and a distal end;
   a cutting balloon coupled to the shaft adjacent the distal end, the cutting balloon having a length; and
   a plurality of cutting members disposed about the balloon;
   wherein four or more wings are defined in the cutting balloon when the balloon is deflated, each of the wings including a pair of undulating side surfaces that extend along substantially the entire length of the balloon and that extend radially outward from the cutting balloon and join at a wing tip, the pair of undulating side surfaces each including a plurality of undulations formed in the balloon that are present when the balloon is deflated prior to use and when the balloon is deflated after use, that are disposed in a regular pattern, and that each include at least one peak and at least one valley, wherein at least one of the wings includes peaks and valleys on one of the undulating side surfaces that are longitudinally-aligned with the peaks and valleys on the other undulating side surface.

4. The device of claim 3, wherein the cutting members and the wings alternate in position about the balloon.

5. The device of claim 3, further comprising a folding spring disposed adjacent a proximal end of the cutting balloon.

* * * * *